US00PP16864P2

(12) United States Plant Patent
Zary

(10) Patent No.: US PP16,864 P2
(45) Date of Patent: Jul. 25, 2006

(54) SHRUB ROSE PLANT NAMED 'JACFABCO'

(50) Latin Name: *Rosa hybrida*
Varietal Denomination: JACfabco

(75) Inventor: Keith W. Zary, Agoura Hills, CA (US)

(73) Assignee: Jackson and Perkins Wholesale, Inc., Medford, OR (US)

( * ) Notice: Subject to any disclaimer, the term of this patent is extended or adjusted under 35 U.S.C. 154(b) by 83 days.

(21) Appl. No.: 10/969,755

(22) Filed: Oct. 19, 2004

(51) Int. Cl.
*A01H 5/00* (2006.01)

(52) U.S. Cl. ..... Plt./103

(58) Field of Classification Search ..... Plt./103, Plt./144, 133
See application file for complete search history.

*Primary Examiner*—Howard J. Locker
(74) *Attorney, Agent, or Firm*—Klarquist Sparkman LLP

(57) ABSTRACT

Shrub rose plant having pure white flowers having a strong fragrance and cupped flower form; strong, disease resistant foliage; and vigorous growth habit on its own roots.

1 Drawing Sheet

Genus and species: *Rosa hybrida.*
Variety denomination: 'JACfabco'.

ORIGIN OF THE INVENTION

The present invention relates to a new and distinct variety of a shrub rose plant named 'JACfabco' which was originated by me by crossing the variety 'JACrex', U.S. Plant Pat. No. 12,130, with the variety 'JACshok', U.S. Plant Pat. No. 11,562.

BACKGROUND OF THE INVENTION

The primary objective of this breeding was to produce a new rose variety having the vigorous growth, clustering ability and strong foliage of the female parent combined with the strong fragrance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Pure white flowers.
2. Strong fragrance.
3. Cupped flower form.
2. Strong, disease resistant foliage.
5. Vigorous growth.
6. Ability to grow on its own roots.

Asexual reproduction of this new variety by cuttings, as performed at Wasco, Calif., shows that the foregoing and all other characteristics and distinctions come true to form and are established and transmitted through succeeding propagations.

Comparison with Parents

As compared to the female parent 'JACrex', 'JACfabco' has about triple the number of petals and has a cupped flower from whereas 'JACrex' has high centered flowers. The male parent 'JACshok' has lavendar flowers having a sweet fragrance whereas 'JACfabco' has white flowers with a strong, citrus fragrance.

Comparison with Similar Variety

A similar variety is 'Iceberg' although 'JACfabco' has much more fragrance, many more petals and a different flower form.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart® 2001, except where ordinary dictionary significance of color is indicated.

Parentage:
*Seed parent.*—'JACrex' (Fabulous!), U.S. Plant Pat. No. 12,130.
*Pollen parent.*—'JACshok' (Cotillion), U.S. Plant Pat. No. 11,562.

FLOWER

Observations made of plants commencing at three years of age in a garden environment at Somis, Calif., from January 2003 to August 2004.

Blooming habit: Continuous.
Bud:
*Size.*—About 35 mm long and 30 mm in diameter when the petals start to unfurl.
*Form.*—The bud form is long, pointed ovoid.
*Color.*—When sepals first divide, bud color is Green-White Group 157A on the bottom third of the bud changing to White Group 155D on the upper twothirds of the bud. When half blown, the upper and lower sides of the petals are White Group 155D.

*Sepals.*—Color: Upper surface: Green Group 138B. Lower surface: Yellow-Green Group 146C. Length: 25 mm. Width: 8 mm. Shape: Subulate. Surface texture: Hoary. There are three lightly appendaged sepals. There are two unappendaged sepals with hairy edges.

*Receptacle.*—Color: Yellow-Green Group 146C but often with Greyed-Red Group 178B in areas exposed to bright sunlight. Shape: Funnel. Size: Medium, about 7 mm long×12 mm wide. Surface: Smooth.

*Peduncle.*—Length: Short, averaging about 5 cm. Surface: Glandular. Color: Yellow-Green Group 146D. Strength: Stiff, erect.

Bloom:

*Size.*—Medium. Average open diameter is about 8 cm.

*Borne.*—Single and several together in pyramidal clusters of 3–5 blooms.

*Stems.*—Strength: Strong. Average length is about 40–50 cm with a diameter of 8–9 mm.

*Form.*—When first open: Cupped. Permanence: Flattens.

*Petalage.*—Number of petals under normal conditions: 150–160.

*Color.*—The upper sides of the petals are White Group 155D. The reverse sides of the petals are White Group 155D. The major color on the upper side is White Group 155D.

*Variegations.*—None observed.

*Discoloration.*—The general tonality at the end of the first day: No change. At the end of the third day: No change.

*Fragrance.*—Strong, citrus (grapefruit).

Petals:

*Texture.*—Thin.

*Shape.*—Round to oblanceolate.

*Surface.*—Smooth.

*Margin.*—Entire. Apex Shape: Rounded. Base Shape: Rounded.

*Form.*—Tips slightly recurved.

*Arrangement.*—Quartered.

*Petaloids.*—Number: None.

*Persistence.*—Petals drop off cleanly before drying.

*Lastingness.*—On the plant: Fair (about 4–5 days). As a cut flower: Short (about 5 days).

Reproductive parts:

*Stamens.*—Number: None observed in 30 flowers observed from 5 plants.

*Pistils.*—Number: 40–45. Length: 8–9 mm. Styles: Color: Yellow-White Group 158D. Length: 7–8 mm. Stigmas: Color: Green-White Group 157C. Length: 1 mm.

*Hips.*—None observed.

PLANT

*Form.*—Shrub.

*Growth.*—Very vigorous, upright, branching.

*Age at maturity.*—Two years.

*Mature plant.*—Height: 150 cm. Width: 120 cm.

*Rootstock.*—Own root.

Foliage: Number of leaflets on normal mid-stem leaves: 5 or 7.

*Size.*—Large. About 14 cm long×8 cm wide.

*Quantity.*—Abundant.

*Color.*—New foliage: Upper side: Greyed-Purple Group 183A. Lower side: Greyed-Purple Group 183A. Old foliage: Upper side: Green Group 139A. Lower side: Green Group 139B.

Leaflets:

*Size.*—About 40 mm long×30 mm wide.

*Shape.*—Pointed oval.

*Base shape.*—Oblique.

*Apex shape.*—Cuspidate.

*Texture.*—Leathery, glossy.

*Edge.*—Serrated.

*Serrations.*—Single.

*Petiole.*—Color: Yellow-Green Group 146B.

*Petiole rachis.*—Color: Yellow-Green Group 146B. Underside: Rough with prickles and glands.

*Stipules.*—Length: 15 mm. Shape: Entire, but edged in glands.

*Disease resistance.*—Resistant to mildew and rust and susceptible to blackspot under normal growing conditions.

*Pest resistance.*—Not observed.

*Vein color.*—Green Group 139B.

*Venation pattern.*—Reticulate.

Wood:

*New wood.*—Color: Greyed-Purple Group 183B. Bark: Smooth.

*Old wood.*—Color: Green Group 137A. Bark: Smooth.

Prickles:

*Quantity.*—On main canes from base: 15 to 18 per 15 cm of stem. On laterals from main canes: 15 to 18 per 15 cm of stem.

*Form.*—Straight.

*Length.*—6–9 mm.

*Color when young.*—Greyed-Purple Group 183A.

*Color when mature.*—Greyed-Orange Group 177A.

Small prickles:

*Quantity.*—On main stalks: None. On laterals: None.

Winter hardiness: Hardy to Zone 5.

I claim:

1. A new and distinct variety of rose plant of the shrub class, substantially as herein shown and described, characterized particularly by its pure white flowers having strong fragrance and cupped flower form; strong, disease resistant foliage; and vigorous growth habit on its own roots.

* * * * *

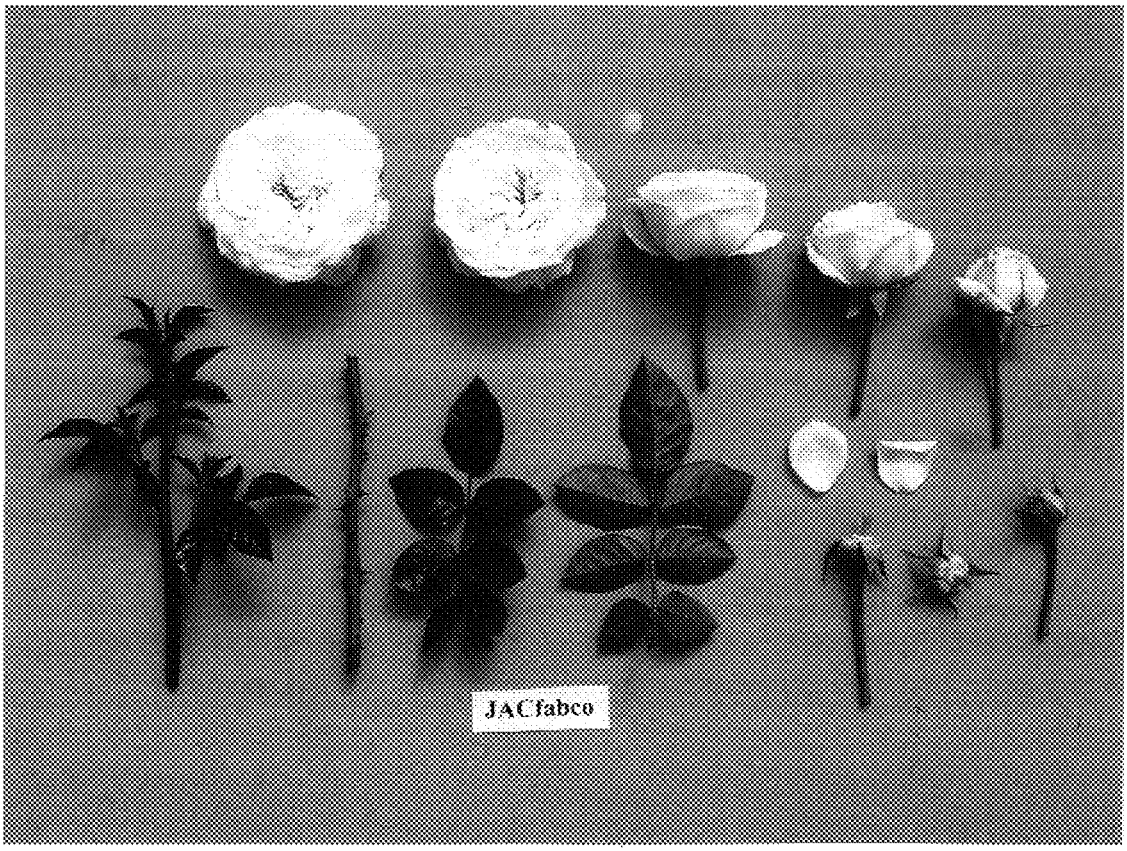
JACfabco

UNITED STATES PATENT AND TRADEMARK OFFICE

CERTIFICATE OF CORRECTION

PATENT NO. : PP 16,864 P2
APPLICATION NO. : 10/969755
DATED : July 25, 2006
INVENTOR(S) : Keith W. Zary It is certified that error appears in the above-identified patent and that said Letters Patent is hereby corrected as shown below:

On Title page item 73
The name of the Assignee is changed from "Jackson and Perkins Wholesale, Inc." to --Jackson & Perkins Wholesale, Inc.--

Signed and Sealed this

Twenty-seventh Day of February, 2007

JON W. DUDAS
*Director of the United States Patent and Trademark Office*